United States Patent [19]

Hawkins et al.

[11] 4,304,592
[45] Dec. 8, 1981

[54] METHOD OF IMPROVING OR MAINTAINING DIGESTIBILITY OF FODDER CROPS

[75] Inventors: Alan F. Hawkins, Woodley; Terence R. Owen, Crowthorne; John S. Morley, Cheadle Hulme; Christopher F. Hayward, Macclesfield, all of England

[73] Assignee: Imperial Chemical Industries Limited, London, England

[21] Appl. No.: 62,226

[22] Filed: Jul. 27, 1979

[30] Foreign Application Priority Data

Aug. 3, 1978 [GB] United Kingdom ............... 32171/78

[51] Int. Cl.$^3$ ............................................. A01N 37/10
[52] U.S. Cl. ..................................... 71/115; 71/107; 562/470
[58] Field of Search .................................. 71/115, 107

[56] References Cited

U.S. PATENT DOCUMENTS

| | | | |
|---|---|---|---|
| 3,240,802 | 3/1966 | Robertson | 562/470 |
| 3,436,206 | 4/1969 | Kinoshita et al. | 71/77 |
| 3,923,491 | 2/1975 | O'Brien et al. | 71/76 |

OTHER PUBLICATIONS

Barrier, Chem. Abst., vol. 71 (1969) 21110s.
Amrhein et al., Ber. Deutsch. Bot. Ges. 89, (1976) S.247-259.
Camm et al., Phytochemistry, vol. 12 (1973) pp. 961–973.

*Primary Examiner*—Catherine L. Mills
*Attorney, Agent, or Firm*—Cushman, Darby & Cushman

[57] ABSTRACT

This invention provides a method of enhancing, or preventing the decline in, the digestibility of a crop, in particular of a fodder crop, by applying to the crop, to seed of the crop, or to the locus of the crop or seed, a compound or a mixture of at least two compounds of general formula (I)

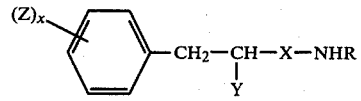

wherein R is hydrogen or —COR$^1$ wherein R$^1$ is alkyl, aryl, aralkyl, alkoxy, aryloxy or aralkyloxy, X is —O—, —NE— or —CH$_2$—, Y is carboxy or an alkali metal, ammonium or mono- or di-alkyl- or cycloalkylamine salt thereof, or Y is alkoxycarbonyl, aryloxycarbonyl, aralkyloxy- carbonyl, amino or mono- or di-alkyl- or aryl- amino, Z is hydrogen, halogen, nitro, alkyl, trihalomethyl, hydroxy, alkoxy, acyloxy, cyano or alkylenedioxy, and x is an integer of 1 to 3. The invention also provides novel compounds, namely L-α-aminooxy-β-(parahydroxy phenyl) propionic acid, and acid addition salts thereof.

9 Claims, No Drawings

METHOD OF IMPROVING OR MAINTAINING DIGESTIBILITY OF FODDER CROPS

The present invention relates to the treatment of crops, such as grasses, legumes (e.g. lucerne and clover), cereals (e.g. barley, wheat and maize), brassicas (e.g. kale), root-crops (e.g. beet). The invention relates, particularly, to fodder crops grown for conservation, either as silage or hay.

Grassland farmers (as well as farmers of other fodder crops) face a difficult decision each year about when to cut their crops for conservation. All grass varieties of agricultural importance suffer from the disadvantage that during the normal increase in dry matter yield with growth, the digestibility decreases. The farmer has, therefore, to compromise between a lower yield of highly digestible material and a higher yield of less digestible material. Another limitation is that harvesting at optimum maturity may be prevented by unfavourable weather. If the decline in digestibility could be controlled or delayed, higher yields of highly digestible material could be obtained and the prevailing weather conditions would not play such a major role in determining the quality of the crop harvested.

We have now found that if fodder crops (or the soil in which they are grown) are treated with certain compounds, as hereinafter defined, their digestibility can be enhanced, or at least a decline in their digestibility can be delayed, and an improved growth yield can be obtained. It is believed that the increase in digestibility is caused by inhibition of lignin formation.

The compounds may be applied to the growing plants, or to the seeds or seedings from which they grow, or to the soil in which they grow or are intended to grow. They may be applied alone, or together with fertilisers, pesticides, fungicides, or similar agricultural and horticultural products.

The present invention accordingly provides a method of treating a crop, for example for enhancing, or preventing the decline in, the digestibility of a fodder crop, the method comprising applying to the crop, to seed of the crop or to the locus of the crop or seed, a compound or a mixture of at least two compounds of general formula (I):

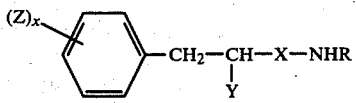

wherein R is hydrogen or $-COR^1$ wherein $R^1$ is alkyl, aryl, aralkyl, alkoxy, aryloxy or aralkyloxy, X is $-O-$, $-NH-$ or $-CH_2-$, Y is carboxy or an alkali metal, ammonium or mono- or di-alkyl- or cycloalkyl- amine salt thereof, or Y is alkoxycarbonyl, aryloxycarbonyl or aralkyloxycarbonyl, Z is hydrogen, halogen, nitro, alkyl, trihalomethyl (e.g. trifluoromethyl), hydroxy, alkoxy, acyloxy, cyano or alkylenedioxy (e.g. methylenedioxy), and x is an integer of 1 to 3, the groups Z being the same or different when X is 2 or 3, and the compound being optionally in the form of an acid addition salt when R is hydrogen.

The compounds of the invention contain chiral centres. The compounds are generally obtained in the form of racemic mixtures. However, these and other mixtures can be separated into the individual isomers by methods known in the art.

The alkyl and alkoxy groups can be straight or branched chain groups having 1 to 6, e.g. 1 to 4 carbon atoms; examples are methyl, ethyl, propyl (n- or iso-propyl), butyl (n-, iso- or t-butyl), methoxy and ethoxy. A suitable cycloalkyl is cyclopentyl or cyclohexyl. The halogen atoms can be fluorine, chlorine, bromine, or iodine.

The aryl groups and the aryl moieties of the aryloxy, aralkyl and aralkyloxy groups can optionally be substituted with for example up to 3 substituents selected from the class consisting of halogen, nitro, alkyl, trihalomethyl (e.g. trifluoromethyl), alkoxy, cyano and alkylenedioxy (e.g. methylenedioxy). A suitable aryl is phenyl and a suitable aralkyl is benzyl.

The group

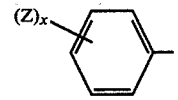

is suitably chlorophenyl (e.g. 2- or 4-chlorophenyl), fluorophenyl (e.g. 4-fluorophenyl), tolyl (e.g. 4-tolyl), hydroxyphenyl, acyloxyphenyl and methoxyphenyl (e.g. 4-methoxyphenyl).

The acid addition salts can be salts with inorganic or organic acids e.g. hydrochloric, hydrobromic, nitric, sulphuric, acetic, p-toluenesulphonic or oxalic acid. The amine salts (when Y is carboxy) can be salts with for example dicyclohexylamine.

Examples of the compounds of general formula (I) are given in Table I.

TABLE I

| COMPOUND | (Z)$_x$ | Y | X | R | PHYSICAL CONSTANT |
|---|---|---|---|---|---|
| 1 | H | COOEt | O | COOEt | b.p. 158–164° C./0.35 mm |
| 2 | 4-Cl | COOEt | O | COOEt | b.p. 175–180° C./0.4 mm |
| 3 | 4-Me | COOEt | O | COOEt | b.p. 143–146° C./0.3 mm |
| 4 | 2-Cl | COOEt | O | COOEt | b.p. 148–151° C./0.3 mm |
| 5 | 4-F | COOEt | O | COOEt | b.p. 148–152° C./0.4 mm |
| 6 | 4-Me | COOH | O | COOEt | m.p. 95–97° C. |
| 7 | 4-F | COOH | O | COOEt | m.p. 104–105° C. |
| 8 | H | COOH | O | COOEt | m.p. 67–69° C. |
| 9* | H | COOH | O | COOCH$_2$Ph | m.p. 156–157° C. |
| 10+ | H | COOMe | O | H | m.p. 133–135° C. |
| 11* | H | COOH | O | COOCH$_2$Ph | m.p. 157–158° C. |
| 12+ | H | COOMe | O | H | m.p. 132–134° C. |
| 13° | H | COOH | O | H | m.p. 144–145° C. |
| 14 | 4-MeO | COOEt | O | COOEt | b.p. 173° C./0.3 mm |
| 15 | 4-MeO | COOH | O | COOEt | gum |
| 16 | 4-MeO | COOH | O | CO . Ph | m.p. 131° C. |

TABLE I-continued

| COMPOUND | (Z)$_x$ | Y | X | R | PHYSICAL CONSTANT |
|---|---|---|---|---|---|
| 17 | 4-MeO | COOEt | O | CO . Ph | m.p. 78–79° C. |
| 18$^x$ | 4-MeO | COOH | O | H | m.p. 150° C. |
| 19** | H | COOH | NH | H | m.p. 218–220° C. |
| 20 | 4-OH | COOH | O | H | M.W. 197.18 |

Notes on Table I
*Compounds 9 and 11 are in the D- and L-forms, respectively
+Compounds 10 and 12 are hydrochloride salts and are in the D- and L-forms, respectively
°Compound 13 is a hydrobromic acid salt and is in the L-form
$^x$Compound 18 is a hydrochloric acid salt
**Compound 19 is in the L-form The compound 20, hereinabove, and acid addition salts thereof, are novel compounds.

The compounds can be applied in a number of ways, for example they can be applied, formulated or unformulated, directly to the foliage of the fodder crops, or they can be applied also to seeds or to other medium in which the crops are growing or are to be planted, or they can be sprayed on, dusted on or applied as a vapour. Application can be to any part of the fodder crops, for example to the foliage or roots, or to soil surrounding the roots, or to the seed before it is planted.

The compounds are preferably used in the form of a composition. The type of composition used in any instance will depend upon the particular purpose envisaged.

The compositions may be in the form of dusting powders or granules comprising the active ingredient and a solid diluent or carrier, for example fillers such as kaolin, bentonite, keiselguhr, dolomite, calcium carbonate, talc, powdered magnesia, Fuller's earth, gypsum, Hewitt's earth, diatomaceous earth and China clay. Such granules can be preformed granules suitable for application to the soil without further treatment. These granules can be made either by impregnating pellets of filler with the active ingredient or by pelleting a mixture of the active ingredient and powdered filler. Compositions for dressing seed, for example, may comprise an agent (for example a mineral oil) for assisting the adhesion of the composition to the seed; alternatively the active ingredient can be formulated for seed dressing purposes using an organic solvent (for example N-methylpyrrolidone or dimethylformamide).

The compositions may also be in the form of dispersible powders, granules or grains comprising a wetting agent to facilitate the dispersion in liquids of the powder or grains which may contain also fillers and suspending agents.

The aqueous dispersions or emulsions may be prepared by dissolving the active ingredient(s) in an organic solvent optionally containing wetting, dispersing or emulsifying agent(s) and then adding the mixture to water which may also contain wetting, dispersing or emulsifying agent(s). Suitable organic solvents are ethylene dichloride, isopropyl alcohol, propylene glycol, diacetone alcohol, toluene, kerosene, methylnaphthalene, the xylenes, trichloroethylene, furfuryl alcohol, tetrahydrofurfuryl alcohol, and glycol ethers (e.g. 2-ethoxyethanol and 2-butoxyethanol).

The compositions to be used as sprays may also be in the form of aerosols wherein the formulation is held in a container under pressure in the presence of a propellant, e.g. fluorotrichloromethane or dichlorodifluoromethane.

The compounds may be used in a microencapsulated form.

By including suitable additives, for example additives for improving the distribution, adhesive power and resistance to rain on treated surfaces, the different compositions can be better adapted for various utilities.

The compositions may also be in the form of liquid preparations for use as dips or sprays which are generally aqueous dispersions or emulsions containing the active ingredient in the presence of one or more surfactants e.g. wetting agent(s), dispersing agent(s), emulsifying agent(s) or suspending agent(s). These agents can be cationic, anionic or non-ionic agents. Suitable cationic agents are quaternary ammonium compounds, for example cetyltrimethylammonium bromide.

Suitable anionic agents are soaps, salts of aliphatic monoesters of sulphuric acid (for example sodium lauryl sulphate), and salts of sulphonated aromatic compounds (for example sodium dodecylbenzenesulphonate, sodium, calcium or ammonium lignosulphonate, butylnaphthalene sulphonate, and a mixture of sodium diisopropyl- and triisopropyl-naphthalene sulphonates).

Suitable non-ionic agents are the condensation products of ethylene oxide with fatty alcohols such as oleyl or cetyl alcohol, or with alkyl phenols such as octyl- or nonyl-phenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example polyvinylpyrrolidone and sodium carboxymethylcellulose), and the vegetable gums (for example gum acacia and gum tragacanth).

The compositions for use as aqueous dispersions or emulsions are generally supplied in the form of a concentrate containing a high proportion of the active ingredient(s), the concentrate to be diluted with water before use. These concentrates often should be able to withstand storage for prolonged periods and after such storage be capable of dilution with water in order to form aqueous preparations which remain homogeneous for a sufficient time to enable them to be applied by conventional spray equipment. The concentrates may conveniently contain up to 95%, suitably 10–85%, for example 25–60%, by weight of the active ingredient(s). These concentrates suitably contain organic acids (e.g. alkaryl or aryl sulphonic acids such as xylenesulphonic acid or dodecylbenzenesulphonic acid) since the presence of such acids can increase the solubility of the active ingredient(s) in the polar solvents often used in the concentrates. The concentrates suitably contain also a high proportion of surfactants so that sufficiently stable emulsions in water can be obtained. After dilution to form aqueous preparations, such preparations may contain varying amounts of the active ingredient(s) depending upon the intended purpose, but an aqueous preparation containing 0.0005% or 0.01% to 10% by weight of active ingredient(s) may be used.

The compounds are suitably applied to the fodder crops at a rate of 1 to 10 kg/ha, preferably about 3 to 5 kg/ha.

The following Examples illustrate the invention. The cellulose digestibilities of the grass samples were determined as follows.

200 mg of the grass sample were placed in a screwcap bottle (volume 25 ml) and treated with 20 ml of cellulase solution (125 mg of cellulase from *Trichoderma viride* in 20 ml of buffer prepared by mixing 93.5 ml of 0.2 M disodium hydrogen phosphate with 106.5 ml of 0.1 M citric acid, adding 40 mg of sodium azide and adjusting the pH to 4.6 if necessary). The bottle was placed in an incubator at 40° C. for 48 hours. The bottle was shaken twice daily. The mixture was filtered through a sintered crucible (porosity No. 1), and the residue was well washed with water and then with acetone. The residue was dried overnight in an oven, cooled and weighed.

EXAMPLE 1

The following experiment was carried out to investigate the effects of Compounds 11, 13 and 19 on the digestibility of maturing grass.

Two species of grass, *Poa annua* and *Setaria viridis*, were used. They were grown in John Innes compost in 10 cm diameter plastic pots, four plants per pot for Setaria and sufficient numbers of Poa to produce a thick sward. The plants were grown for approximately 6 weeks under warm (25°–27° C.), illuminated, glasshouse conditions. They were cut once and fertilised with the fertiliser SOLUFEED [nitrogen 17.50%, water-soluble phosphoric acid 10.00% (calculated as $P_2O_5$) and potash 13.50% (calculated as $K_2O$)] to encourage tillering and formation of a thick stand. The plants were top-watered but subjected to some water-stress to encourage maturation. As soon as flower spike initiation was observed, the plants were sprayed with the test compounds. The compounds were applied at a rate equivalent to 4 kg/ha of active ingredient (formulated in cyclohexanone) and the formulation was applied at a spray volume equivalent to 200 l/ha. Five replicate pots were set up per treatment. At 9 and 16 days after treatment, the foliage was cut at soil level and fresh weights and dry weights measured. The cellulase digestibility was determined as described above.

The yield and digestibility results for Setaria and Poa are given in Tables II and III, respectively.

TABLE II

| TREATMENT | FRESH WEIGHT (g/pot) | DRY MATTER CONTENT (%) | DRY MATTER YIELD (g/pot) | CELLULASE DIGESTIBILITY (%) | DIGESTABLE DRY MATTER YIELD (g/pot) |
|---|---|---|---|---|---|
| 9-Day Harvest | | | | | |
| Control | 10.2 | 13.8 | 1.41 | 68.8 | 0.97 |
| 13 | 12.2 | 13.0 | 1.59 | 72.8* | 1.16 |
| 11 | 11.0 | 13.5 | 1.49 | 72.3 | 1.08 |
| 19 | 11.4 | 13.9 | 1.58 | 68.0 | 1.07 |
| 16-Day Harvest | | | | | |
| Control | 15.2 | 16.8 | 2.55 | 59.1 | 1.51 |
| 13 | 16.2 | 16.2 | 2.62 | 63.0** | 1.65 |
| 11 | 16.3 | 16.5 | 2.69 | 61.4 | 1.65 |
| 19 | 16.3 | 15.6 | 2.54 | 60.6 | 1.54 |

*significant increase compared with control
** highly significant increase compared with control

TABLE III

| TREATMENT | FRESH WEIGHT (g/pot) | DRY MATTER CONTENT (%) | DRY MATTER YIELD (g/pot) | CELLULASE DIGESTIBILITY (%) | DIGESTIBLE DRY MATTER YIELD (g/pot) |
|---|---|---|---|---|---|
| 9-Day Harvest | | | | | |
| Control | 18.5 | 16.6 | 3.06 | 65.1 | 2.00 |
| 13 | 23.9** | 14.0 | 3.34 | 70.0** | 2.34** |
| 11 | 20.9* | 15.5 | 3.23 | 65.8 | 2.13 |
| 19 | 22.9** | 15.3 | 3.50** | 70.7** | 2.47** |
| 16-Day Harvest | | | | | |
| Control | 23.3 | 16.7 | 3.89 | 63.2 | 2.46 |
| 13 | 21.2 | 17.6 | 3.70 | 67.5** | 2.50 |
| 11 | 23.5 | 17.3 | 4.05 | 64.6 | 2.62 |
| 19 | 22.8 | 18.8** | 4.26* | 67.0** | 2.85** |

*significant increase compared with control
**highly significant increase compared with control The compounds tested showed a tendency to increase the yield of material harvested per pot. With both grasses, there were consistent increases in cellulase digestibility, several of which were significant at P=5 or 1%. There were consistent increases in digestible dry matter per pot and with Poa several of these results were significant (P=1%).

A feature common to all grass varieties of agricultural importance is that, during the normal increase in yield of dry matter with growth, the yield of digestible organic matter reaches a maximum. Thus as the crop matures, the digestible organic matter is effectively diluted with indigestible material and the overall digestibility of the crop decreases. This decrease in digestibility is brought about by the formation of lignin which not only is indigestible itself but also binds cellulosic material in an indigestible form. Thus the effect on digestibility of a small increase in the lignin content of the plant may be more marked than would be expected from this small increase in indigestible lignin. The practical effect is that the grassland farmer, when deciding when to cut the crop for ensilage, has to make a compromise between a smaller yield of highly digestible material and a higher yield of less digestible material. Thus, using the example of Green, Corrall and Terry [Grassland Research Institute (Hurley) Technical Report No 8 of February 1971], if S23 perennial ryegrass is cut on May 20th, the average dry matter yield would be 6.1 t/ha and the average D value would be 70 while if cutting was delayed until June 5th, the average dry matter yield would be 9.1 t/ha with an average D value of 65. Therefore, although the dry matter yield is increased by 3 t/ha and in fact the yield of digestible organic matter is increased from 4.3 to 5.9 t/ha, the later cut material is of a lower quality and may therefore cause a dry matter intake problem when fed to dairy cattle. If the lignin content of the crop could be prevented from increasing, thus holding the crop for an extended period at its original D value of 70, an additional 3 t/ha of high quality crop would be produced.

The results from these experiments indicate that these lignification inhibiting agents have a practical effect on crop digestibility. For example, with Poa, the digestibility of crop cut 16 days after being treated with two of the compounds was higher than that of untreated material cut 7 days previously and significantly higher than that of control material cut at the same time.

EXAMPLE 2

A pot culture experiment was carried out in 15 cm diameter pots, equipped with water tubes, and using Frensham soil. Each pot was sown with 1 g 'Delecta' Italian Ryegrass seed (this variety was selected for its ability to flower without vernalisation). After germination the grass was subjected to a day length of 16 hours (supplementing natural light by the light of mercury vapour lamps).

A preliminary grass cut was taken to produce an even 'sward' and all of the pots were treated with a basal application of NPK fertiliser as $NH_4NO_3$, monoammonium phosphate, and KCl, respectively. The grass was then allowed to grow to a height of about 30 cm. Six replicate pots were harvested to determine dry matter yield and digestibility (using the cellulase assay described above) at the time of spraying. Six further replicates were sprayed with a formulation of compound 19 (hydrazine analogue of phenylalanine) at a rate equivalent to 4 kg active ingredient/ha. A further six pots were untreated. The grass in the pots was then grown in the glasshouse, under lights, for 5 weeks. The six treated pots and the six untreated pots were then harvested, the grass dry matter yield and the digestibility of the grass were then determined. The results are shown in the following Table IV. (All figures are the mean of six replicates):

TABLE IV

| | DRY MATTER YIELD (g/pot) | CELLULASE DIGESTIBILITY (%) |
|---|---|---|
| Control (cut at spraying) | 13.2 | 67.8 |
| Control (cut 5 weeks after spraying) | 120.5 | 59.7 |
| Treated with compound 19 (cut 5 weeks after spraying) | 119.9 | 66.0 |

There was a highly significant decline in the digestibility of the untreated grass over the 5 weeks growth period, but the decline in digestibility of the treated grass was much less. This difference in digestibility of the treated and untreated grass after 5 weeks was highly significant.

As mentioned above, the compounds may be applied in admixture. A suitable mixture comprises the novel compound L-α-aminooxy-β-(parahydroxy phenyl) propionic acid (compound 20) or an acid addition salt thereof in admixture with L-α-aminooxy-β-phenyl propionic acid (compound 13) or an acid addition salt thereof.

The present invention also provides novel compounds of general formula I, wherein $(Z)_x$ is —OH, Y is —COOH, X is —O— and R is —H, namely L-α-aminooxy-β-(parahydroxy phenyl) propionic acid, and acid addition salts thereof.

EXAMPLE 3

A solution of L-α-benzyloxycarbonylaminoxy-β-(p-benzyloxyphenyl)propionic acid (1.26 g.) in HBr(acetic acid (47% w/v; 2 ml.) was kept at room temperature for 2 hours. The resulting suspension was diluted with ether and the resulting precipitate was washed with ether and dried in vacuo over KOH and $P_2O_5$ to give L-α-aminoxy-β-(p-hydroxyphenyl)propionic acid hydrobromide (0.61 g.). The product had the following n.m.r. spectrum (δ) in $d_6$ dimethyl sulphoxide using tetramethylsilane as an internal standard (δ=0): 2.5 (multiplet, 2H); 4.0 (multiplet, 1H); 5.6, 5.85 (multiplets, 4H); 7.0 (broad, exchangeable hydrogens).

The hydrobromide was dissolved in water and applied to a column of AG50 WX2 in H+ form. The column was washed with water and then with 1 M aqueous ammonia. The basic eluate was evaporated to dryness and the residue dissolved in ethanol. This solution was evaporated to dryness and the residue dissolved in isopropanol. This solution was evaporated and the residue triturated with ether to give the free aminoxyacid as a white solid which was washed with ether and dried at 40° C. in vacuo. This product was a single spot on various thin layer chromatography systems.

The L-α-benzyloxycarbonylaminoxy-β-(p-benzyloxyphenyl)propionic acid used as starting material may be obtained as follows:

To a solution of D-O-benzyltyrosine (8.14 g.) in acetic acid (300 ml.) and water (60 ml.) was added KBr (21.4 g.) and the mixture stirred at 0°–5° C. A solution of $NaNO_2$ (4.15 g.) in water (10 ml.) was added dropwise over 30 minutes to this cooled reaction mixture. The resulting solution was stirred for a further 2 hours at room temperature. The solvent was evaporated and the residue triturated with water to give an oil. This was extracted into ethyl acetate (2×100 ml.) and the combined extracts washed with water (6×25 ml.) and dried ($MgSO_4$). The solvent was evaporated to give a solid which was purified by chromatography on a silica column using cyclohexane/ethyl acetate (1:1 v/v) as eluant. The isolated product, D-α-bromo-β-(p-benzyloxyphenyl)propionic acid (6 g.) crystallised when triturated with warm petroleum ether (b.p. 60°–80° C.).

To a suspension of sodium hydride (1.08 g. of an 80% w/w dispersion in oil) in dimethylformamide (25 ml.) at 0° C. was added N-benzyloxycarbonylhydroxylamine (3 g.) in dimethylformamide (10 ml.) in small portions. When effervescence ceased, a solution of D-α-bromo-β-p-benzyloxyphenyl)propionic acid (6 g.) in dimethylformamide (10 ml.) was added slowly. The mixture was stirred at 0° C. for 30 minutes and then overnight at room temperature. The solvent was evaporated and the residue diluted with water. The resulting suspension was acidified to pH 3 with dilute aqueous HCl and the solid extracted into ethyl acetate (2×200 ml.). The combined extracts were washed with water (4×50 ml.), dried (MgSO₄) and evaporated to give an oil. This was purified by chromatography on a silica column using chloroform/methanol/acetic acid 96:3:1 v/v/v as solvent. Two main fractions were obtained, the second being the required product. It was crystallised from cyclohexane to give L-α-benzyloxycarbonylaminoxy-β-(p-benzyloxyphenyl)-propionic acid (3.96 g.).

We claim:

1. A method of treating a crop for enhancing, or delaying the decline in, the digestibility of a fodder crop, the method comprising applying to the crop, to seed of the crop, or to the locus of the crop or seed, at least one compound selected from compounds of the formula:

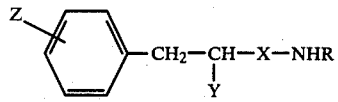

wherein
R is hydrogen or COR' wherein R' is phenyl, alkoxy of 1-6 carbons, or benzyloxy;
X is —O— or —NH—;
Y is carboxy or alkoxycarbonyl wherein the alkoxy contains 1-6 carbons; and
Z is hydrogen, halogen, hydroxy or alkoxy of 1-6 carbons,
and acid addition salts thereof when R is hydrogen.

2. A method as claimed in claim 1, wherein the compound is N-benzyloxy-carbonyl-L-α-aminooxy-β-phenyl propionic acid.

3. A method as claimed in claim 1, wherein the compound is L-α-aminooxy-β-phenyl propionic acid.

4. A method as claimed in claim 3, wherein the compound is a hydrobromic acid salt of L-α-aminoocy-β-phenyl propionic acid.

5. A method as claimed in claim 1, wherein the compound is L-α-hydrazine-β-phenyl propionic acid.

6. A method as claimed in claim 1, wherein the compound is L-α-aminooxy-β-(parahydroxy phenyl) propionic acid or acid addition salt thereof.

7. A method as claimed in claim 1, comprising applying to the crop, to seed of the crop or to the locus of the crop or seed a mixture of L-α-aminooxy-β-(parahydroxy phenyl) propionic acid, or an acid addition salt thereof, with L-α-aminooxy-β-phenyl propionic acid, or an acid addition salt.

8. A method as claimed in claim 1, wherein the compound or mixture of compounds is applied at a rate of 1 to 10 Kg/ha.

9. A method as claimed in claim 8, wherein the compound or mixture of compounds is applied at a rate of 3 to 5 Kg/ha.

* * * * *